US006187534B1

(12) United States Patent
Strom et al.

(10) Patent No.: US 6,187,534 B1
(45) Date of Patent: *Feb. 13, 2001

(54) METHODS OF EVALUATING TRANSPLANT REJECTION

(75) Inventors: Terry B. Strom; Lauro Vasconcellos, both of Brookline, MA (US); Manikkam Suthanthiran, New York, NY (US)

(73) Assignees: Cornell Research Foundation, Inc., Ithaca, NY (US); Beth Israel Deaconess Medical Center, Boston, MA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/937,063

(22) Filed: Sep. 24, 1997

(51) Int. Cl.[7] .................................................. C12Q 1/68
(52) U.S. Cl. ......................... 435/6; 435/7.24; 536/24.31
(58) Field of Search ............................. 435/6, 29, 7.24; 536/24.31, 24.33

(56) References Cited

U.S. PATENT DOCUMENTS 5,213,961  5/1993  Bunn et al. .

FOREIGN PATENT DOCUMENTS

PCT/US98/19549  2/1999  (WO) .

OTHER PUBLICATIONS

B. Guerette et al., "Increased Granzyme B mRNA after Alloincompatible Myoblast Transplantation," *Transplantation*, 60(9):1011–1016 (Nov. 15, 1995).
H. Robertson et al., "Renal Allograft Rejection–in situ Demonstration of Cytotoxic Intratubular Cells," *Transplantation*, 61(10):1546–1556 (May 1996).
Rush, D.N. et al., "Histological Findings in Early Routine Biopsies of Stable Renal Allograft Recipients," *Transplantation* 57(2): 208–211 (1994).
Rush, D.N. et al., "Sequential Protocol Biopsies in Renal Transplant Patients: Clinico–pathological Correlations Using the Banff Schema," *Transplantation* 59(4): 511–514 (1995).
Pavlakis, M. et al., "Use of Intragraft Gene Expression in the Diagnosis of Kidney Allograft Rejection," *Transplantation Proceedings*, 28(4): 2019–2021 (1996).
Larsen, C.P. et al., "Fas–mediated Cytotoxicity: An Immunoeffector or Immunoregulatory Pathway in T Cell–Mediated Immune Responses?," *Transplantation* 60(3): 221–224 (1995).

Lipman, M. et al., "Cytokine Gene Transcripts are Prevalent in Protocol Biopsies From Stable Renal Allografts," *J. of the American Society of Nephrology*, A3208/S614(PS),vol. 7(9): 1888 (1996). (Abstract).
Lipman, M. et al., "Cytokine Transcript Expression in Sequential Renal Allograft Biopsies is Dynamic," *J. of the American Soc Nephrology*, A3209/S613 (PS) 7(9): 1888 (1996). (Abstract).
Lipman, M. et al., "Cytokine and Cytotoxic T Lymphocyte (CTL)Transcript Levels in "Surveillance" Renal Biopsies by Quantitative PCR," *J. of the American Society of Nephrology*, 6:1060 (1995).
Matsuno, T. et al., "Expression of Intercellular Adhesion Molecule–1 and Perforin on Kidney Allograft Rejection," *Transplant. Proc.* 24(4): 1306–1307 (1992).
Grimm, P.C. et al., "Low Frequency of Infiltrating Cells Intensely Expressing T Cell Cytokine mRNA in Human Renal Allograft Rejection," *Transplantation* 59(4): 579–584 (1995).
O'Connell, P.J. et al., "Unmodified Pancreatic Islet Allograft Rejection Results in the Preferential Expression of Certain T Cell Activation Transcripts," *J. Immunol.* 150(3): 1093–1104 (1993).
Strom, T.B. et al., "The Th1/Th2 Paradigm and the Allograft Response," *Curr. Opin. Immunol.* 8(5): 688–693 (1996).
Griffiths, G.M. et al., "Granzyme A and Perforin as Markers for Rejection in Cardiac Transplantation," *Eur. J. Immunol.*, 21:687–692 (1991).
Meyer–König, U. et al., "Human Cytomegalovirus Immediate Early and Late Transcripts in Peripheral Blood Leukocytes: Diagnostic Value in Renal Transplant Recipients," *J. Infectious Diseases*, 171:705–709 (1995).
Strehlau, J. et al., "Quantitative Detection of Immune Activation Transcripts as a Diagnostic Tool in Kidney Transplantation," *Proc. Natl. Acad. Sci. USA*, vol. 94:695–700 (1997).
Cassol, S.A. et al., "Primer–Mediated Enzymatic Amplification of Cytomegalovirus (CMV) DNA: Application to the Early Diagnosis of CMV Infection in Marrow Transplant Recipients," *J. Clin. Invest.*, vol. 83(4):1109–1115 (1989).
Remick, Daniel G., "Clinical Applications of Molecular Biology," at 165–174 in *Clinical Laboratory Medicine*, McClatchey, K.D. ed, Williams & Wilkins, Baltimore, MD (1994).

(List continued on next page.)

*Primary Examiner*—Patrick J. Nolan
(74) *Attorney, Agent, or Firm*—Beth E. Arnold; M. Sharon Webb; Foley, Hoag & Eliot LLP (57) ABSTRACT

The invention relates to methods of evaluating transplant rejection in a host comprising determining a heightened magnitude of gene expression of two out of three immune activation marker genes perforin, granzyme B and Fas ligand, in a tissue biopsy or peripheral blood mononuclear cell sample, particularly using reverse transcription polymerase chain reaction; methods of assessing antirejection therapy; and kits for use in evaluating transplant rejection.

23 Claims, 3 Drawing Sheets

OTHER PUBLICATIONS

Mueller, C. et al., "The Effect of Cyclosporine Treatment on the Expression of Genes Encoding Granzyme A and Perforin in the Infiltrate of Mouse Heart Transplants," *Transplantation*, 55: 139–145 (1993).

Lipman, M.L. et al., "Heightened Intragraft CTL Gene Expression in Acutely Rejecting Renal Allografts," *J. Immunol.* 152:5120–5127 (1994).

Clément, M.V. et al., "Perforin and Granzyme B as Markers For Acute Rejection in Heart Transplantation," *Int. Immunol.*, vol. 3(11): 1175–1181 (1991).

Clément, M.V. et al., "Perforin and Granzyme B Expression Is Associated With Severe Acute Rejection," *Transplantation*, 57: 322–326 (1994).

Kummer, J.A. et al., "Expression of Granzyme A and B Proteins by Cytotoxic Lymphocytes Involved in Acute Renal Allograft Rejection," *Kidney Int.*, 47:70–77 (1995).

Sunder–Plassmann, G. et al., "Upregulation of a Lymphoid Serine Protease in Kidney Allograft Recipients," *Kidney Int'l.*, 37: 1350–1356 (1990).

McDiarmid, S.V. et al., "Perforin and Granzyme B: Cytolytic Proteins Up–Regulated During Rejection of Rat Small Intestine Allografts," *Transplantation* 59(5):762–766 (1995).

Vasconcellos, L. et al., "Rantes and IL–8: Intragraft Chemokine Transcript Expression in Human Renal Allografts," *Journal Amer. Soc. Nephrology*, A3257/5600 (PS) 7(9):1898 (1996).

Strehlau, J. et al., "The Intragraft Gene Activation of Markers Reflecting T–cell–activation and–Cytotoxicity Analyzed by Quantitative RT–PCR in Renal Transplantation," *Clinical Nephrology*, 46(1):30–33 (1996).

Stehlau, J. et al., "Cytotoxic Lymphocyte (CTL) Specific Gene Expression as a Rapid and Highly Accurate Tool to Identify Rejecting Renal Allografts," *Nephrolophrology Dialysis Transplantation*, vol. 11(6):A288 (1996).

Strehlau, J. et al., "IL–15 and IL–7 but not IL–2 Gene Expression is Heightened in Rejecting Renal Allografts," *Nephrology Dialysis Transplantation*, 11(6):A288 (1996).

Legros–Maida, S. et al., "Granzyme B Perforin Can be Used as Predictive Markers of Acute Rejection in Heart Transplantation," *Eur. J. Immunol.* 24: 229–233 (1994).

Wright, P.A. and D. Wynford–Thomas, "The Polymerase Chain Reaction: Miracle or Mirage? A Critical Review of its Uses and Limitations in Diagnosis and Research," *J. Pathol.162*: 99–117 (1990).

Pavlakis, M. et al., "Intragraft Expression of T–cell Activation Genes in Human Renal Allograft Rejection," *Kidney Int. Suppl.* 53: S7–12 (Jan. 1996).

Manfro, R.C. et al., "Interleukin–15 Gene Transcripts are Present in Rejecting Islet Allografts," *Transplant Proc.* 29(1–2): 1077–8 (Feb.–Mar. 1997).

Pavlakis, M. et al., "Intragraft IL–15 Transcripts are Increased in Human Renal Allograft Rejection," *Transplantation* 62(4): 543–5 (Aug. 27, 1996).

Suthanthiran, M., "Clinical Application of Molecular Biology: A Study of Allograft Rejection with Polymerase Chain Reaction," *Am. J. Med. Sci.* 313(5):264–7 (May 1997).

Suthanthiran, M., "Acute Rejection of Renal Allografts: Mechanistic Insights and Therapeutic Options," *Kidney Int.* 51(4):1289–1304 (Apr. 1997).

Sharma, V.K. et al., "Intragraft TGF–β 1 mRNA: A Correlate of Interstitial Fibrosis and Chronic Allograft Nephropathy," *Kidney Int.* 49(5):1297–1303 (May 1996).

Pavlakis, M. et al., "Intragraft T–cell Receptor Transcript Expression in Human Renal Allografts," *J. Am. Soc. Nephrol.* 6(2):281–5 (Aug. 1995).

Suthanthiran, M. "Molecular Analyses of Human Renal Allografts: Differential Intragraft Gene Expression During Rejection," *Kidney Int. Supp.* 58: S15–S21 (Mar. 1997).

Jeyarajah, Transplantation Proceedings, vol. 27: 887–889, 1995.*

* cited by examiner

Fig. 1

| gene | size cDNA and CT | method for CT | oligonucleotide size | oligonucleotide direction | oligonucleotide sequence 5' to 3' | gene acc. no. |
|---|---|---|---|---|---|---|
| GAPDH | 496 / 442 | enzyme Hpa II | 20 / 20 | sense / antisense | GGTGAAGGTCGGAGTCAACG / CAAAGTTGTCATGGATGACC | J04038 |
| IL-2 | 149 / 178 | insert DNA | 20 / 20 | sense / antisense | CCTCTGGAGGAAGTGCTAAA / ATGGTTGCTGTCTCATCAGC | K02056 |
| IL-4 | 227 / 159 | primer deletion | 21 / 22 | sense / antisense | TTCTACAGCCACCATGAGAAG / CAGCTCGAACACTTTGAATAT | M23442 |
| IL-7 | 516 / 418 | 4-primer | 25 / 21 | sense / antisense | TTAGGTATATCTTTGGACTTCCTC / GTGTTCTTTAGTGCCCATCAA | J04156 |
| IL-8 | 271 / 242 | double sense | 22 / 25 | sense / antisense | TCTCTTGGCAGCCTTCCT / AATTCTCAGCCTCTTCAAAAACTT | M68932 |
| IL-10 | 617 / 518 | enzyme SspI | 18 / 18 | sense / antisense | GCCGTGGAGCAGGTGAAG / AAGCCCAGACAAGATA | X78437 |
| IL-15 | 409 / 339 | enzyme BstBI | 20 / 19 | sense / antisense | CCGTGGCTTTGAGTAATGAG / CAGATTCTGTACATTCCC | X91233 |
| IL-17 | 471 / 416 | enzyme EcoO109 I | 17 / 17 | sense / antisense | GGAGGCCATAGTGAAGG / GGGTCGGCTCTCCATAG | U32659 |
| perforin | 369 / 267 | enzyme Ava II | 17 / 18 | sense / antisense | CGGCTCACACTCACAGG / CTGCCGTGGATGCCTATG | M31951 |
| granzyme B | 431 / 358 | enzyme Dde I | 24 / 24 | sense / antisense | GGGGAAGCTCCATAAATGTCACCT / TACACACAAGAGGGCCTCCAGAGT | M28879 |
| Fas-Ligand | 321 / 236 | 4-primer | 18 / 18 | sense / antisense | GCCTGTGTCTCCTTGTGA / GCCACCCTTCTTCTATACTT | U11821 |
| TGF-β1 | 246 / 290 | insert DNA | 20 / 20 | sense / antisense | CTGCGGATCTCTGTGTCATT / CTCAGAGTGTTGCTATGGTG | X14885-91 |
| IFN-γ | 510 / 422 | enzyme Alu I | 22 / 22 | sense / antisense | CCAGAGCATCCAAAAGAGTGTG / CTAGTTGGCCCTGAGATAAAG | A02137 |
| CTLA4 | 529 / 459 | 4-primer | 20 / 22 | sense / antisense | GCAATGCACGTGGCCCAGCC / TTTCACATTCTGGCTCTGTTGG | M28879 |
| Rantes | 239 / 204 | double sense | 20 / 19 | sense / antisense | CGGCACGCCTCGCTGTCATC / TGTACTCCCGAACCCATTT | M21121 | bp 100 200 300 400 500 600

Fig. 2F ived and chronic rejection in adults and children, many advocate
METHODS OF EVALUATING TRANSPLANT REJECTION

BACKGROUND OF THE INVENTION

Despite recent improvements in renal allograft survival, the loss of graft function due to acute and chronic rejection continues and is a leading cause of end-stage renal failure today. As the occurrence of acute rejection episodes is the most powerful predictive factor for the later development of chronic rejection in adults and children, many advocate strategies to detect and ablate acute rejection episodes as early as possible.

Procedures to diagnose renal allograft rejection depend upon detection of graft dysfunction and the presence of a mononuclear leukocytic infiltrate. However, the presence of a modest cellular infiltrate is often not conclusive and can be detected in non-rejecting grafts. It would be helpful to have a reliable tool for diagnosis and follow-up of acute renal allograft rejection.

SUMMARY OF THE INVENTION

The present invention relates to methods of monitoring the status of a transplanted organ in a host. More specifically, the present invention relates to evaluating transplant rejection in a host comprising determining the magnitude of gene expression of the immune activation markers perforin (P), granzyme B (GB), and Fas ligand (FasL) genes, in a post-transplant biological sample obtained from the host and comparing the relative expression of the marker genes to a baseline level of expression of the immune activation marker, wherein upregulation of gene expression (i.e., increased or heightened gene expression) of two of the three immune activation marker genes in the sample indicates rejection. Immune activation genes are also referred to herein as cytotoxic lymphocyte (CTL) effector molecules. The methods described herein are particulary useful to detect acute transplant rejection.

Most typically, the host (i.e., the recipient of a transplant) is a mammal, such as a human. The transplanted organ can include any transplantable organ or tissue, for example kidney, liver, heart, lung or bone marrow.

The post-transplant biological sample (or test sample) from the host can be any biological sample comprising cells that contain RNA (i.e., transcripts) encoding the immune activation marker genes of interest. For example, the sample can be a tissue biopsy sample, or a peripheral blood sample containing mononuclear cells. Additionally, the sample can be lymphatic fluid, peritoneal fluid or pleural fluid. The tissue biopsy sample can be allograft tissue or xenograft tissue. In one embodiment of the present invention, the sample is obtained from a renal allograft.

The magnitude of expression of the immune activation marker genes is determined by quantifying immune activation marker gene transcripts and comparing this quantity to the quantity of transcripts of a constitutively expressed gene. The term "magnitude of expression" means a "normalized, or standardized amount of gene expression". For example, the overall expression of all genes in cells varies (i.e., is not constant). The observation of the increased expression of a gene, as determined by an increase in the presence of an mRNA transcript, must be put into the proper context to accurately assess whether the detection of increased transcript is significant. That is, there must be some way to "normalize" gene expression to accurately compare levels of expression between samples. This can be accomplished by determining the level of expression of the gene of interest (e.g., determining gene mRNA or cDNA transcribed from the gene mRNA) and the level of expression of a universally, or constitutively expressed gene (e.g., a gene that is present in all tissues and has a constant level of expression), and comparing the relative levels of expression between the target gene (gene of interest) and the constitutively expressed gene. In one embodiment, the constitutively expressed gene is glyceraldehydrate-3-phosphate dehydrogenase (GAPDH). Other constitutively expressed genes, such as actin, are known to those of skill in the art and can be suitable for use in the methods described herein. In the methods described herein, quantification of gene transcripts was accomplished using competitive reverse transcription polymerase chain reaction (RT-PCR) and the magnitude of gene expression was determined by calculating the ratio of the quantity of gene expression of each immune activation marker gene to the quantity of gene expression of the constitutively expressed gene. That is, the magnitude of target gene expression is calculated as pg of target gene cDNA per pg of constitutively-expressed gene cDNA.

In one embodiment, the discriminatory level for heightened gene expression (e.g., the baseline magnitude of gene expression) of the immune activation marker gene is set to the mean ±95% confidence interval of a group of values observed in nonrejecting transplants (e.g., control values). Heightened gene expression is determined as above a mean ±95% confidence interval of these values.

In another embodiment, sequential samples can be obtained from the host and the quantification of immune activation gene markers determined as described herein, and the course of rejection can be followed over a period of time. In this case, for example, the baseline magnitude of gene expression of the immune activation marker genes is the magnitude of gene expression in a post-transplant sample taken very shortly after the transplant. For example, an initial sample or samples can be taken within the nonrejection period, for example, within one week of transplantation and the magnitude of expression of marker genes in these samples can be compared with the magnitude of expression of the genes in samples taken after one week. In one embodiment, the samples are taken on days 0, 3, 5, 7 and 10.

In another embodiment, the post-transplant test sample comprises a blood sample obtained from the host which contains peripheral blood mononuclear cells (PBMCs) which is evaluated for the immune activation gene markers. Additionally, the PBMC sample is substantially simultaneously, or sequentially, evaluated for the presence or absence of one or more genes that are characteristic of (e.g., a marker for) an infectious agent (e.g., a virus). In this embodiment, heightened gene expression of two of the three immune activation marker genes, P, GB and FasL, concomitant with the absence of the marker for the infectious agent indicates transplant rejection. For example, to evaluate transplant rejection of a renal allograft, the genes characteristic of the infectious agent cytomegalovirus (CMV) would be assessed. Importantly, this embodiment acts as a screening test, using easily obtained PBMCS, to differentially distinguish between acute rejection of the transplant or infection. In this case, further testing, such as with a transplant biopsy sample, will only be performed if the initial "screening" test using PBMCs is positive for rejection. Thus, transplant hosts are not submitted to invasive biopsy procedures unless it is justified (i.e., necessary to establish rejection).

In one embodiment, the biological sample is prepared for evaluation by isolating RNA from the sample, using methods described herein, and deriving (obtaining) complementary DNA (cDNA) from the isolated RNA by reverse transcription techniques. However, other methods can be used to obtain RNA, and these methods are known to those of skill in the art.

Commercially available kits for use in these methods are also known to those of skill in the art. For example, in one embodiment described herein, PBMCs are isolated from whole blood and RNA is extracted using a commercially available QIAGEN™ technique. For example, QIAGEN manufactures a number of commercially available kits for RNA isolation, including RNEASY® Total RNA System (involving binding total RNA to a silica-gel-based membrane and spinning the RNA); OLIGOTEX™ mRNA kits (utilizing spherical latex particles); and QIAGEN total RNA kit for In Vitro Transcripts and RNA clean-up. The basic QIAGEN technique involves four steps, as set forth in Example 2, below. The QIAGEN technique can be modified to enhance the RNA isolation, by methods well-known to those of skill in the art.

The complementary DNA was coamplified with a gene-specific competitor and the quantification comprised generating a standard curve of serial dilutions of the gene-specific competitor with a constant amount of control reverse transcribed complementary DNA, thereby enabling quantification of the transcript of the gene of interest. As described herein, the gene-specific competitor is generated from phytohemagglutinin-simulated blast cells or nephrectomy tissue.

For example, the cDNA of perforin can be amplified with a pair of oligonucleotide primers comprising the nucleotides of SEQ. ID. NOS.:17 and 18 of Table 1. Likewise, the transcript of glyceraldehydrate-3-phosphate dehydrogenase can be amplified with oligonucleotide primers comprising the nucleotide sequence of SEQ. ID. NOS. 1 and 2. Although these primers are specifically described herein, other suitable primers can be designed using techniques well-known to those of skill in the art. See, for example, *Current Protocols in Molecular Biology*, Volume 2, Ausubel et al., eds., John Wiley & Sons, Inc. (1997) at pp. 15.0.1-1-15.8.8.

The methods described herein are useful to assess the efficacy of anti-rejection therapy. Such methods involve comparing the pre-administration magnitude of the transcripts of the marker genes to the post-administration magnitude of the transcripts of the same genes, where a post-administration magnitude of the transcripts of the genes that is less than the pre-administration magnitude of the transcripts of the same genes indicates the efficacy of the anti-rejection therapy. Any candidates for prevention and/or treatment of transplant rejection, (such as drugs, antibodies, or other forms of rejection or prevention) can be screened by comparison of magnitude of marker expression before and after exposure to the candidate. In addition, valuable information can be gathered in this manner to aid in the determination of future clinical management of the host upon whose biological material the assessment is being performed. The assessment can be performed using a biological sample (such as a biopsy or PBMCs) from the host, using the methods described herein for determining the magnitude of gene expression of the marker genes. Analysis can further comprise detection of an infectious agent.

The present invention also relates to kits for evaluating transplant rejection. For instance, the kits can include such components as means to aid in RNA isolation, cDNA derivation, RT-PCR, quantification of gene expression, and detection of an infectious agent. In one embodiment, a kit for detecting the presence of transplant rejection in a blood sample comprises means for determining the magnitude of expression of perforin, granzyme B, Fas ligand, and GAPDH in the sample and means for determining the presence of infectious agent transcripts in the sample. For example, the kit can comprise oligonucleotide primers comprising SEQ ID NOS: 1, 2, 17, 18, 19, 20, 21 and 22. The kit can also contain other primers which can be designed using methods well-known to those of skill in the art.

Thus, as a result of the work described herein, methods are now available to accurately quantitate immune activation gene expression in biopsy tissue and peripheral blood mononuclear cells and to correlate the magnitude of expression of these genes with rejection allografts. Specifically, the evaluation of three immune activation genes in a biopsy tissue, perforin, granzyme B and Fas ligand, and determination of heightened gene expression of two of three of these genes accurately diagnoses acute allograft rejection. Surprisingly, the evaluation of the expression of these marker genes in PBMCs, along with the evaluation of expression of an infectious agent gene, also accurately detects allograft rejection.

BRIEF DESCRIPTION OF THE DRAWINGS

FIG. 1 is a chart that depicts the size and sequences (SEQ ID NOS: 1–30) of oligonucleotide primers and competitive templates (CTs) used for the quantification of 15 genes. Deletions and insertions are indicated by black and white portions of bars, respectively.

DETAILED DESCRIPTION OF INVENTION

Renal transplantation is the treatment of choice for patients afflicted with end-stage renal disease, one of the ten leading causes of death in the United States. However, about 20–25% of the first and 30–35% of the second cadaveric renal allografts fail within one year of transplantation, despite recent advances in organ preservation, histocompatibility testing and immunosuppressive strategies.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

ACUTE ALLOGRAFT REJECTION

The single most common cause for early graft failure, especially within one month post-transplantation, is immunologic rejection of the allograft. The unfavorable impact of the rejection is magnified by the fact that: (a) the use of high-dose anti-rejection therapy, superimposed upon maintenance immunosuppression, is primarily responsible for the morbidity and mortality associated with transplantation, (b) the immunization against "public" HLA-specificities resulting from a rejected graft renders this patient population difficult to retransplant and (c) the return of the immunized recipient with a failed graft to the pool of patients awaiting transplantation enhances the perennial problem of organ shortage.

As used herein, "transplant rejection" is defined as functional and structural deterioration of the organ due to an active immune response expressed by the recipient, and independent of non-immunologic causes of organ dysfunction.

The diagnosis of renal allograft rejection is made usually by the development of graft dysfunction (e.g., an increase in the concentration of serum creatinine) and morphologic evidence of graft injury in areas of the graft also manifesting mononuclear cell infiltration. Two caveats apply, however, to the use of abnormal renal function as an indicator of the rejection process: first, deterioration in renal function is not always available as a clinical clue to diagnose rejection since many of the cadaveric renal grafts suffer from acute (reversible) renal failure in the immediate post-transplantation period due to injury from harvesting and ex-vivo preservation procedures. Second, even when immediate renal function is present, graft dysfunction might develop due to a non-immunologic cause, such as immunosuppressive therapy itself.

For example, cyclosporine (CsA) nephrotoxicity, a complication that is not readily identified solely on the basis of plasma/blood concentrations of CsA, is a common complication. The clinical importance of distinguishing rejection from CsA nephrotoxicity cannot be overemphasized since the therapeutic strategies are diametrically opposite: escalation of immunosuppressants for rejection, and reduction of CsA dosage for nephrotoxicity.

The differentiation of the diagnosis of rejection from other etiologies for graft dysfunction and institution of effective therapy is further complicated because: (a) the percutaneous core needle biopsy of renal graft, the best of available current tools to diagnose rejection is performed usually after the "fact", i.e., graft dysfunction and graft damage (irreversible in some instances) are already present, (b) the morphological analysis of the graft provides modest clues with respect to the potential for reversal of a given rejection episode, and minimal clues regarding the likelihood of recurrence ("rebound"), and (c) the mechanistic basis of the rejection phenomenon, a prerequisite for the design of therapeutic strategies, is poorly defined by current diagnostic indices, including morphologic features of rejection.

Antigen-triggered T-cell activation and the subsequent infiltration of activated CD4+ and CD8+ T-cell clones, macrophages, and natural killer (NK) cells into the graft are key events of acute allograft rejection. Although a T-cell-rich interstitial nephritis is a hallmark of acute allograft rejection, clinical rejection episodes responsive to treatment often show only a modest cellular infiltrate and similar infiltrates are observed in surveillance biopsies obtained in well-functioning renal allografts (Rush et al., *Transplantation* 57: 208–211 (1994)); (Rush et al., *Transplantation* 59: 511–514 (1994)).

The present invention relates to the discovery that clinical rejection is associated with expression of a specific subset of T-cell-dependent immune activation genes that serve as a diagnostic indicator of rejection. Patterns of intragraft mRNA generation during a cytopathic allograft response are substantially different from those seen in other causes of graft dysfunction and may provide timely and specific information about immune events relevant to graft rejection.

More specifically, as described herein, the combined analysis of three immune activation or gene markers, perforin (P), granzyme B (GB), and Fas ligand (FasL), provides a reliable tool for the evaluation (e.g., detection, or diagnosis and follow-up) of acute cellular renal allograft rejection. The determination of increased gene transcripts of any two of these three genes indicates transplant rejection. For example, a detectable increase in gene expression of perforin and granzyme B in a kidney tissue biopsy sample, with no detectable increase in Fas ligand gene expression, is indicative of transplant rejection.

Perforins and granzyme B are proteins present in the granules of cytotoxic T lymphocytes (CTLs). Perforins are pore-forming molecules that can polymerize and perforate the cell membrane. Granzymes are a family of serine proteases that colocalizes with performs in the CTL cytoplasmic granules. The entry of granzyme B into the target cell via perforin-created channels results in apoptosis of the target cell. Perforin-independent pathways of cell-mediated cytolysis, such as the interaction between Fas (APO1) antigen and Fas ligand (FasL), have been implicated in $Ca^{2+}$-independent systems in which the perforin monomer is unable to polymerize but cell-mediated cytolosis still occurs. Pavlakis, M. *Transplant. Proc.* 28(4):2019–2021 (1996).

FasL/Fas receptor-mediated CTL injury initiates target cell death via a $Ca^{2+}$-independent apoptotic pathway. Intragraft FasL expression, noted during murine cardiac allograft rejection, Larsen et al, *Transplantation* 60:221–224 (1995), has not previously been investigated in clinical transplantation.

These immune activation gene markers can be obtained from a biological sample of the host. The sample can be a tissue biopsy sample (e.g., a kidney biopsy sample), or a blood sample containing peripheral blood mononuclear cells (PBMCs).

As used herein, the term "biopsy" refers to a specimen obtained by removing tissue from living patients for diagnostic examination. The term includes aspiration biopsies; brush biopsies; chorionic villus biopsies; endoscopic biopsies; excision biopsies; needle biopsies (specimens obtained by removal by aspiration through an appropriate needle or trocar that pierces the skin, or the external surface of an organ, and into the underlying tissue to be examined); open biopsies; punch biopsies (trephine); shave biopsies; sponge biopsies; and wedge biopsies. In one embodiment, a fine needle aspiration biopsy is used. In another embodiment, a minicore needle biopsy is used. A conventional percutaneous core needle biopsy can also be used.

As described herein, the combined analysis of three immune activation genes, FasL, P, and GB, resulted in statistically significant detection of transplant rejection as compared with an analysis of any individual gene transcript. Heightened gene expression of at least two of the three CTL genes is detected only in specimens from kidneys undergoing acute cellular rejection, while low expression of these genes was confined to biopsies with other causes of graft dysfunction. Elevated IL-15, FasL, and P, but not IL-7, IL-10, or GB, transcripts were occasionally found in the few chronic rejection samples processed. This finding suggests a linkage between the causation of acute and chronic rejection.

It is important to note that the mere existence of a mononuclear leukocytic infiltrate, the hallmark for the histopathological diagnosis of rejection, may not necessarily be harmful for a transplant. Sequential biopsies obtained from well-functioning renal allografts at 3 and 6 months have frequently shown mononuclear leukocytic infiltrates (Rush et al., *Transplantation* 57: 208–211 (1994)); (Rush et al., Transplantation 59: 511–514 (1994)) without heightened expression for cytokines, P, or GB (Lipman et al., *J. Am. Soc. Nephrol.* 6: 1060 (1995)). Nonetheless, some of these grafts have developed subsequent chronic rejection (Rush et al., *Transplantation* 59: 511–514 (1994)). In one experimental system, an effective cyclosporine regimen did not prevent graft infiltration, but such treatment lowered the frequency of CD8+ cells expressing P and G (Mueller et al., *Transplantation* 55: 139–145 (1993)). In accordance with the notion that many graft-infiltrating T-cells are not cytodestructive, in histological sections of rejecting human renal allografts only few T cells show P mRNA expression (Matsuno et al., *Transplant. Proc.* 24: 1306–1307 (1992); Grimm, P. C. et al., *Transplantation* 59: 579–584 (1995). The number of borderline cases examined by the methods described herein support the concept that a case of a mild cellular infiltrate rejection can be identified by immune activation gene expression analysis.

As described in Example 1, simultaneous analysis of intragraft gene expression of CTL effector molecules identified acute rejection (AR) in renal allografts with extraordinary sensitivity and specificity and can be introduced as a reliable diagnostic tool in the clinical management of renal transplant patients.

The methods described herein use competitive reverse transcription (RT)-PCR to evaluate the diagnostic accuracy of multiple immune activation gene analysis as a means to diagnose renal allograft rejection. The magnitude of intragraft gene expression of 15 immune activation genes was quantified by competitive RT-PCR in 60 renal allograft core biopsies obtained for surveillance or to diagnose the etiology of graft dysfunction. The sequences of oligonucleotide primers and competitive templates that were used are shown in FIG. 1 and Table 1. The results were compared with a clinicopathological analysis based upon the histological diagnosis (Banff criteria) and the response to antirejection treatment.

During acute renal allograft rejection, intragraft expression of the genes of interleukin (IL)-7 (P<0.001), IL-10 (P<0.0001), IL-15 (P<0.0001), Fas ligand (P<0.0001), perforin (P<0.0001), and granzyme B (P<0.0015), but not IL-2, interferon γ, or IL-4, was significantly heightened. Amplified RANTES and IL-8 gene transcripts are sensitive but non-specific markers of rejection. A simultaneous RT-PCR evaluation of perforin, granzyme B, and Fas ligand identified acute rejection, including cases with mild infiltration, with extraordinary sensitivity (100%) and specificity (100%). Effective antirejection therapy resulted in a rapid downregulation of gene expression. Heightened gene expression of chemokines (IL-8, RANTES), non-T-cell-derived T-cell growth factors (IL-7, IL-15) and CTL-selective effector molecules was observed during rejection.

Thus, the quantitative RT-PCR analysis of intragraft IL-10 and IL-15 transcripts (macrophages) and the CTL-selective genes P, GB, and FasL provided a reliable and highly sensitive tool for the diagnosis of acute renal allograft rejection. RANTES and IL-8 transcripts proved to be sensitive but nonspecific indicators of rejection. IL-7 and IL-17 transcripts were seen only in rejection, but false negatives were commonplace. IL-2 and IL-4 gene expression were not detected in rejection samples, while expression of IFN-γ, TGF-β1, and CTLA4 genes was not selective for rejection.

Figure 2A:
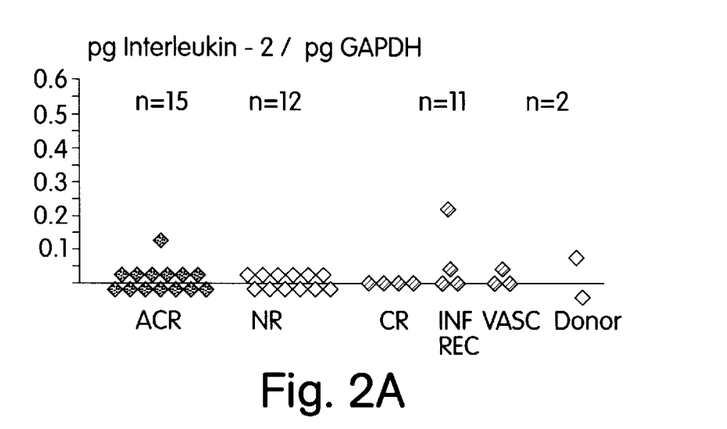
FIGS. 2A–F are graphs that depict the quantitative analysis of IL-2, IL-7, IL-15, perforin (P), granzyme B (GB), and Fas Ligand (FasL) gene expression in 38 transplant core biopsies taken to aid in the differential diagnosis of graft dysfunction. Biopsies were also obtained from two donor kidneys prior to reperfusion. Lines indicate sequential biopsies taken during the course of rejection before and after treatment (ACR, acute cellular rejection; NR, nonrejecting kidneys with acute tubular necrosis or cyclosporine cytotoxicity; CR, chronic rejection; INF REC, infectious complications and recurrence of primary disease; and VASC, vascular complications).
Figure 2B:
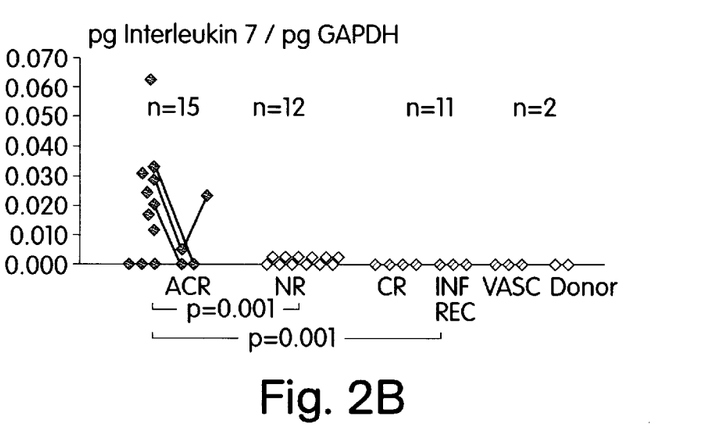
Figure 2C:
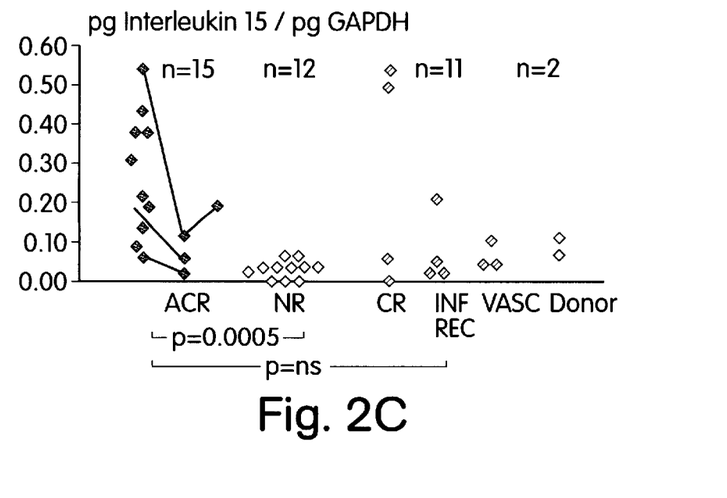
Figure 2D:
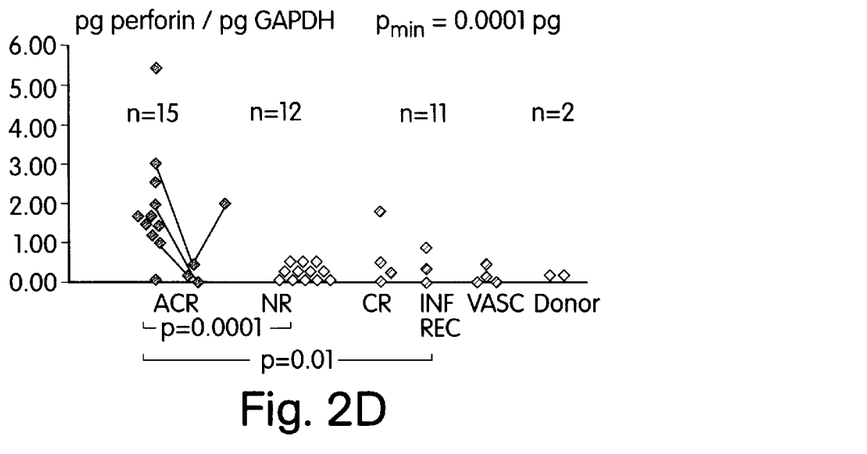
Figure 2E:
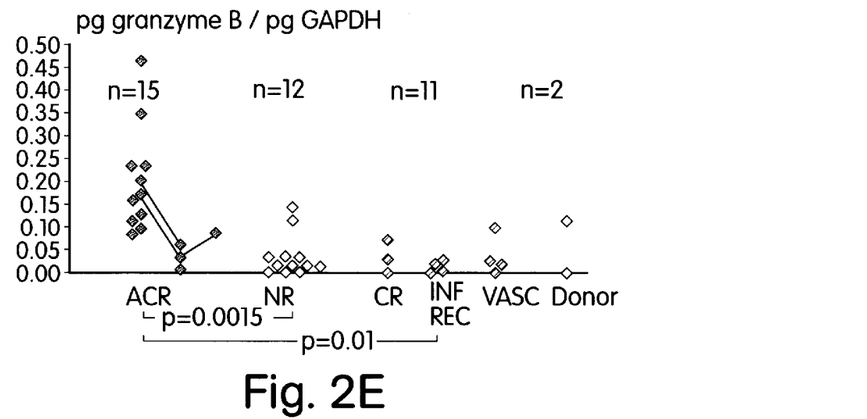
Figure 2F:
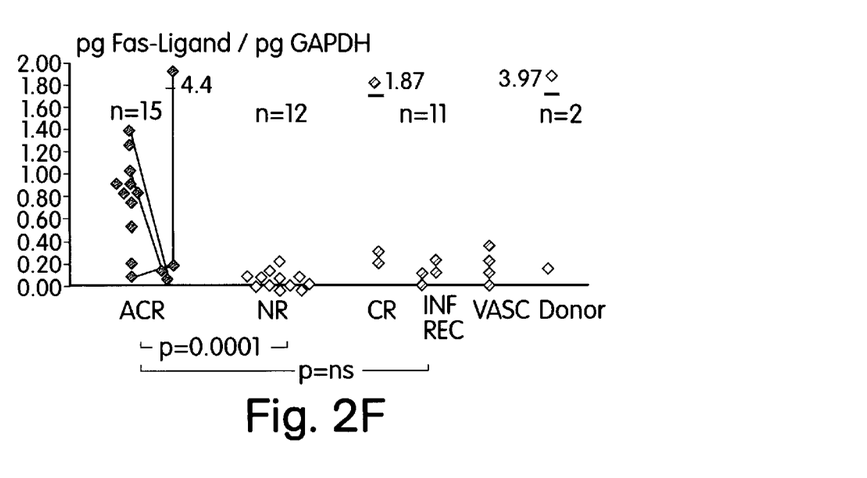

Further, the data described herein suggest that muted IL-7, IL-10, IL-15, and CTL gene expression can serve as an indicator for effective antirejection therapy (FIG. 2). This effect may occur by gene regulation or cell elimination.

IL-2 and IL-4 were not detected during rejection episodes. An ongoing surveillance biopsy study may determine whether (i) IL-2 gene expression precedes clinically evident rejection as noted in preclinical models (O'Connell et al., *J. Immunol.* 150: 1093–1104 (1993)) and (ii) IL-4 gene expression is detectable in long-term stable allografts. IL-4 gene expression frequently accompanies successful long-term engraftment in preclinical trials (Strom et al., *Curr. Opin. Immunol.* 8: 688–693 (1996)).

Also as described herein, methods using RT-PCR with RNA isolated from peripheral blood mononuclear cells, or PMBCs, for gene expression of perforin (P), granzyme B(GB) and Fas-ligand (FasL), also accurately detected acute rejection. The results, described in Example 2, established that the expression of these transcripts in PBMCs and core biopsy tissue correlated and this expression also correlated with the histological diagnosis. More specifically, transplant rejection can be tested in PBMCs by evaluating the magnitude of expression of the immune activation markers P, GB and FasL, and additionally detecting the presence or absence of an infectious agent.

As used herein, an "infectious agent" refers to any agent which plays a role in infection in a graft patient. Infectious agents include bacteria such as *Escherichia coli*, Klebsiella, Enterobacteriaceae, Pseudomonas, and Enterococcus; Fungi, such as *Candida albicans, Histoplasma capsulatum*, and Cryptococcus; viruses such as Hepatitis B and C viruses, human immunodeficiency virus, and herpes-group viruses, which include herpes simplex virus type 1, herpes simplex virus type 2, varicella-zoster virus (VZV), cytomegalovirus (CMV), Epstein-Barr virus (EBV), Human Herpesvirus 6, Human Herpesvirus 7, Kaposi's Sarcoma-associated virus (human herpesvirus 8), and Papovaviruses; and parasites, including, but not limited to, *Plasmodium falciparum, Toxoplasma gondii*, strongyloides, stercoralis, and *Trypanosoma cruzi*.

In one embodiment, the infectious agent analyzed is cytomegalovirus (CMV). CMV is a common and dangerous infection in transplant recipients. It generally appears on or after the end of the first post-transplant month. 50% of all renal transplant recipients presenting with fever 1 to 4 months after transplantation have evidence of CMV disease. *Harrison's Principles of Internal Medicine*, 14th. ed. Fauci, A. S. et al., McGraw-Hill (1988). CMV itself accounts for the fever in more than $\frac{2}{3}$ of cases and thus is the predominant pathogen during this period. CMV infection may also present as arthralgias or myalgias. This infection can result in primary disease (in the case of a seronegative recipient who receives a kidney from a seropositive donor) or can present as either reactivation disease or superinfection during this interval. CMV also causes glomerulopathy and is associated with an increased incidence of other opportunistic infections (e.g., fungal infection). Because of the frequency and severity of CMV disease, considerable effort has been made to attempt to prevent and treat it in renal transplant recipients. CMV retinitis can also appear as a late infection (more than 6 months after transplantation). Furthermore, active CMV infection is sometimes associated, and confused, with transplant rejection episodes.

As described in Example 2, false positive PBMC results indicating acute transplant rejection were obtained from two patients with CMV infection. Therefore, additionally detecting the presence or absence of one or more genes characteristic of CMV can effectively discriminate between acute rejection and CMV infection. For example, in addition to quantifying CDNA encoding perforin, granzyme B and Fas ligand, determining the presence or absence of cDNA encoding a gene characteristic of CMV (or other infectious agent) can be simultaneously, or subsequently determined by RT-PCR. The genetic properties of cytomegalovirus have been characterized in great detail, and are well known to those of skill in the art. (See, for example, *Virology*, 2$^{nd}$ Ed., Fields, B. N. E., Raven Press, Ltd., N.Y. (1990)), at pages 1595–2010. Primer sequences for CMV are known and available to those of skill in the art. See Meyer König, U. et al. *J. Infectious Diseases*, Vol. 171:705–709 (1995) the contents of which are incorporated by reference in their entirety; Wright, P. A. and D. Wynford-Thomas, *J. Pathol.*, Vol. 162:99 (1990); Cassol, S. A. et al, *J. Clin. Invest.*, Vol. 83:1109–1115 (1989). For example, primer sequences TCC ACG CTG TTT TGA CCT CCA TAG (CMV-sense) (SEQ ID NO:31) and GAC ATC TTT CTC GGG GTT CTC GTT (CMV anti-sense) (SEQ ID NO:32) can be used. Competitive templates can be devised to accurately quantify CMV and other infectious agents transcripts using the methods described herein for the immune activation marker genes. See Clinical Laboratory Medicine, McClatchey, K. D., ed., William & Wilkins, Baltimore, Md. (1994) at 165–174.

Other transplants, including lung, heart, liver and bone marrow, can be tested in a similar matter. For example, embodiment, detection of hepatitis virus transcripts can effectively discriminate between liver transplant rejection and hepatitis infection. One of skill in the art can design primers for detection of hepatitis virus use in this embodiment. See *Virology*, supra, at pages 1981–2236.

As a result of the data described herein, methods are now available for the rapid and reliable diagnosis of acute rejection, even in cases with only mild cellular infiltrates. Described herein for the first time, analysis of immune activation genes transcripts obtained from PBMCs, with additional analysis of CMV transcripts, accurately detect transplant rejection. Using the methods described herein, additional early warning markers may be identified in order to utilize the sensitivity and specificity of RT-PCR to elucidate specific patterns of gene activation in vascular, chronic, and treatment-resistant rejections by refining the diagnostic criteria.

The present invention will now be illustrated by the following examples, which are not intended to be limiting in any way.

EXAMPLE 1: ANALYSIS OF BIOPSY SAMPLES
BIOPSIES

Sixty kidney transplant biopsies were investigated for gene expression of chemokines (IL-8, RANTES (regulated upon activation, normal T-cell expressed and secreted), T-cell growth factors and other cytokines (IL-2, IL-4, IL-7, IL-10, IL-15, and IL-17), cell surface immunoregulatory proteins (CTLA4), cytotoxic effector molecules (P, GB, FasL), IFN-γ, transforming growth factor (TGF)-β1, and the housekeeping protein glyceraldehyde-3-phosphate dehydrogenase (GAPDH). Thirty-eight biopsies were obtained from 34 patients (25 adults and 9 children) to clarify the cause of graft dysfunction, 20 for early post-transplant surveillance and 2 from living related donor kidneys prior to reperfusion. Small portions of biopsy cores ($1/10$–$1/2$) were immediately snap frozen in liquid nitrogen at the bedside and stored at 70° C. The majority of tissue was used for histopathological analysis. Biopsies obtained to evaluate the cause of graft dysfunction were classified according to the Banff criteria (Solez et al., *Kidney Int.* 44: 411–422 (1993)) as rejection (pretreatment n=12, post-treatment n=3), nonrejection (acute tubular necrosis, cyclosporine nephrotoxicity n=12), chronic rejection (n=3), recurrence of primary disease (n=4), or other complications (n=4). In 4 of 12 rejecting samples and 4 of 12 acute tubular necrosis samples a mild cellular infiltrate was observed (borderline cases) and the diagnosis of rejection was confirmed by a beneficial clinical response to corticosteroids or OKT3 treatment.

RNA ISOLATION

Procedures for isolation of tissue RNA and reverse transcription into cDNA were performed as described in detail (Lipman et al., *J. Immunol.* 152: 5120–5127 (1994)). In brief, total RNA was isolated by tissue homogenization in guanidine isothiocyanate/2-mercaptoethanol and ultracentrifugation in CsCl. One microgram of RNA was reverse transcribed by Moloney murine leukemia virus transcriptase and diluted to a final volume of 40 µl.

QUANTIFICATION OF GENE EXPRESSION BY COMPETITIVE TEMPLATE RT-PCR

Expression of specific gene transcripts identified within biopsy tissue was quantified by competitive RT-PCR as described in Lipman, M., et al.,*J. Immunol.*, 152:5120–5127 (1994), the contents of which is incorporated herein in its entirety by reference. Competitive RT-PCT is also described in Bunn et al. (U.S. Pat. No. 5,213,961, incorporated herein by reference in its entirety). The CDNA derived from biopsy samples was coamplified with a known amount of a mutated target gene CDNA fragment—the gene-specific competitor. Sense and antisense oligonucleotides proportionately amplified both competitor and reverse-transcribed cDNA sequences in accordance with their relative initial abundance in the PCR. (Sequences are listed in FIG. 1 and Table 1 as SEQ ID NOS: 1–30).

TABLE 1

Sequences of oligonucleotide primers and competitive templates (CTs) used for the quantitation of 15 genes evaluated.

| GENE | DIRECTION | SEQUENCE 5' TO 3' | SEQ. ID. NO. | GENE ACC |
|---|---|---|---|---|
| GAPDH | sense | GGTGAAGGTCGGAGTCAACG | SEQ. ID. NO:1 | J04038 |
|  | antisense | CAAAGTTGTCATGGATGACC | SEQ. ID. NO:2 |  |
| IL-2 | sense | CCTCTGGAGGAAGTGCTAAA | SEQ. ID. NO:3 | K02056 |
|  | antisense | ATGGTTGCTGTCTCATCAGC | SEQ. ID. NO:4 |  |
| IL-4 | sense | TTCTACAGCCACCATGAGAAG | SEQ. ID. NO:5 | M23442 |
|  | antisense | CAGCTCGAACACTTTGAATAT | SEQ. ID. NO:6 |  |
| IL-7 | sense | TTTAGGTATATCTTTGGACTTCCTC | SEQ. ID. NO:7 | J04156 |
|  | antisense | GTGTTCTTTAGTGCCCATCAA | SEQ. ID. NO:8 |  |
| IL-8 | sense | TCTCTTGGCAGCCTTCCT | SEQ. ID. NO:9 | M68932 |
|  | antisense | AATTCTCAGCCTCTTCAAAAACTT | SEQ. ID. NO:10 |  |

TABLE 1-continued

Sequences of oligonucleotide primers and competitive templates (CTs) used for the quantitation of 15 genes evaluated.

| GENE | DIRECTION | SEQUENCE 5' TO 3' | SEQ. ID. NO. | GENE ACC |
|---|---|---|---|---|
| IL-10 | sense | GCCGTGGAGCAGGTGAAG | SEQ. ID. NO:11 | X78437 |
|  | antisense | AAGCCCAGAGACAAGATA | SEQ. ID. NO:12 |  |
| IL-15 | sense | CCGTGGCTTTGAGTAATGAG | SEQ. ID. NO:13 | x91233 |
|  | antisense | CAGATTCTGTTACATTCCC | SEQ. ID. NO:14 |  |
| IL-17 | sense | GGAGGCCATAGTGAAGG | SEQ. ID. NO:15 | U32659 |
|  | antisense | GGGTCGGCTCTCCATAG | SEQ. ID. NO:16 |  |
| perforin | sense | CGGCTCACACTCACAGG | SEQ. ID. NO:17 | M31951 |
|  | antisense | CTGCCGTGGATGCCTATG | SEQ. ID. NO:18 |  |
| granzyme B | sense | GGGGAAGCTCCATAAATGTCACCT | SEQ. ID. NO:19 | M28879 |
|  | antisense | TACACACAAGAGGGCCTCCAGAGT | SEQ. ID. NO:20 |  |
| Fas-L | sense | GCCTGTGTCTCCTTGTGA | SEQ. ID. NO:21 | U11821 |
|  | antisense | GCCACCCTTCTTATACTT | SEQ. ID. NO:22 |  |
| TGF-β1 | sense | CTGCGGATCTCTGTGTCATT | SEQ. ID. NO:23 | X14885–91 |
|  | antisense | CTCAGAGTGTTGCTATGGTG | SEQ. ID. NO:24 |  |
| IFN-γ | sense | CCAGAGCATCCAAAAGAGTGTG | SEQ. ID. NO:25 | A02137 |
|  | antisense | CTAGTTGGCCCCTGAGATAAAG | SEQ. ID. NO:26 |  |
| CTLA4 | sense | GCAATGCACGTGGCCCAGCC | SEQ. ID. NO:27 | M28879 |
|  | antisense | TTTCACATTCTGGCTCTGTTGG | SEQ. ID. NO:28 |  |
| RANTES | sense | CGGCACGCCTCGCTGTCATC | SEQ. ID. NO:29 | M21121 |
|  | antisense | TGTACTCCCGAACCCATTT | SEQ. ID. NO:30 |  |

The PCR products were separated by agarose gel electrophoresis, stained with ethidium bromide, photographed in UV light with Polaroid type 55 positive/negative film, and scanned by laser densitometry (LKB Ultrascan). The ratio of densities (competitive template (CT)/reverse-transcribed cDNA) reflects the initial amounts of cDNA added (pg of competitive template per pg of reverse-transcribed cDNA). Standard curves were generated by serial dilutions of the gene-specific competitors with a constant amount of control reverse transcribed cDNA, thereby enabling quantification of the wild-type gene transcript.

Contaminating genomic DNA was easily identified by size differences, as all oligonucleotide probes were targeted to separate exons of the gene of interest. The conditions used for all competitive PCRs were identical: 94° C. for 30 sec, 55° C. for 20 sec, 72° C. for 20 sec, 10-min extension at 72° C. after 35 cycles (Perkin-Elmer Cetus 480).

Competitors from phytohemagglutinin-stimulated blasts or nephrectomy tissue were generated by four different techniques (FIG. 1): (i)excision of a 50- to 100-bp fragment in the center of the target gene cDNA by using appropriate restriction enzymes (GAPDH, IFN-γ, IL-10, IL-15, IL-17, P, and GB); (ii) amplification of external parts of the cDNA by two separate PCRs and religation of these fragments (CTLA4, IL-7, FasL);(iii) insertion of a short DNA fragment into the target sequence (IL-2, IL-4, TGF-1, or primer deletion (IL-4)); and (iv) one-step generation of a shortened DNA sequence by use of a specifically designed double-sense primer. Competitors were cloned in a TA vector (Invitrogen, San Diego), transfected into DH5a cells (Promega), purified, and quantitated by UV spectrometry.

Amplification of the universally expressed GAPDH gene served to confirm successful RNA isolation and reverse transcription. The magnitude of target gene expression was calculated as pg of target gene CDNA per pg of GAPDH cDNA.

Statistical analysis was performed using a Newman-Keuls test for normally distributed data or a Kruskal-Wallis test.

RESULTS

The small amount of tissue available for this study ($\frac{1}{10}$ to $\frac{1}{2}$ of a biopsy core) proved to be sufficient for a thorough analysis of gene expression. The RNA yield ranged from 1 to 20 μg, depending on the size of the biopsy fragment, allowing 40–800 PCRs per sample. A quantitative analysis of gene expression was necessary, because low levels of transcripts are detectable in many biopsies, while heightened expression of select genes occured only during rejection (FIG. 2A–F, Table 2).

TABLE 2

Quantitative analysis of intragraft gene expression for 15 immune activation genes.

| Gene | Rejection | Nonrejection | P* | Sensitivity % | Specificity % |
|---|---|---|---|---|---|
| IL-2 | 0.0 | 0.0 | NS | 8 | NA |
| IL-4 | 0.0 | 0.0 | NS | 0 | 0 |
| TGF-β1 | 112 ± 87 | 98 ± 78 | NS | 45 | 55 |
| CTLA-4 | 577 ± 396 | 228 ± 214 | <0.057 | 60 | 70 |
| RANTES | 284 ± 147 | 132 ± 104 | <0.064 | 91 | 71 |
| IFN-γ | 214 ± 194 | 151 ± 130 | 0.007 | 75 | 67 |
| IL-17 | 24 ± 12 | 0.0 | <0.001 | 83 | 75 |
| IL-7 | 38 ± 40 | 0.0 | <0.001 | 83 | 100 |
| IL-8 | 112 ± 82 | 67 ± | <0.0005 | 100 | 67 |
| IL-10 | 451 ± 340 | 24 ± 30 | <0.0005 | 83 | 89 |
| IL-15 | 236 ± 162 | 85 ± 37 | <0.0005 | 83 | 92 |
| GB | 174 ± 94 | 46 ± 51 | <0.0015 | 91 | 86 |

TABLE 2-continued

Quantitative analysis of intragraft gene expression for 15 immune activation genes.

| Gene | Rejection | Nonrejection | P* | Sensitivity % | Specificity % |
|------|-----------|--------------|------|------|------|
| P    | 1705 ± 1021 | 338 ± 410  | <0.0001 | 83 | 92 |
| FasL | 779 ± 360   | 120 ± 101  | <0.0001 | 83 | 92 |

Values are given as mean±SD pg of target gene CDNA per pg of GAPDH CDNA. The intensity of intragraft expression of individual CTL genes was compared with histologic (Banff) criteria for establishing the diagnosis of graft rejection through an analysis of 40 transplant biopsies and, in borderline cases, clinical response to antirejection treatment. NA, not applicable.

* Statistical analysis was performed with a Newman-Keuls test for normally distributed data and a Kruskal-Wallis test for others. NS, not significant.

Heightened gene expression during acute rejection was detected for IL-7, IL-8, RANTES, IL-10, IL-15, IL-17, CTLA4, and all three CTL effector molecules, e.g., GB, P, and FasL (FIG. 2A–F). GB and IL-10 expression (P<0.0015 and P<0.0005) proved to be significant and specific markers of acute, but not chronic, rejection, while IL-15 (P<0.0015), FasL, and P (P<0.0001 and P<0.0001) transcription was augmented during acute allograft rejection and in some of the chronic rejection samples analyzed. The magnitude of expression of individual CTL-specific genes was not linked, and no evidence was found that the granula-dependent (GB, P) or the receptor-mediated (FasL) pathways were alternatively activated. IL-7 and IL-17 transcripts were solely, but not reliably, observed in rejecting samples, while an increase of IL-8 and RANTES mRNA was found in both rejection and graft dysfunction related to other causes. The highest level of any target gene expression measured was 4.4 times higher than the amount of GAPDH gene expression in this sample (FasL in an acute rejection episode). IL-2 and IL-4 gene expression did not accompany rejection episodes.

The accuracy of this PCR-based molecular approach to verify rejection can be considerably enhanced by a simultaneous analysis of CTL gene expression (Table 3). If a discriminatory level for heightened gene expression is set to the mean ±95% confidence interval of values observed in nonrejecting kidneys (maximum 0.07 pg/pg of GAPDH for GB, 0.4 pg/pg of GAPDH for FasL, and 0.8 pg/pg of GAPDH for P), the combined analysis of all three CTL effector molecules identifies acute cellular rejection, including borderline cases with a sensitivity of 100% and a specificity of 100% in our series (P<0.0001).

TABLE 3

Combined analysis of CTL gene expression

| Gene | Rejection | Nonrejection | P* | Sensitivity % | Specificity % |
|------|-----------|--------------|------|------|------|
| P + GB, one or both up-regulated | 11/12 | 5/28 | 0.00015* | 91 | 82 |
| FasL + GB, one or both up-regulated | 12/12 | 4/28 | <0.0001 | 100 | 85 |
| FasL + GB + P, any two up-regulated | 12/12 | 0/28 | <0.0001* | 100 | 100 |

Expression of an individual gene was deemed positive for values above the mean ±95% confidence interval of nonrejecting kidneys (maximum 0.07 pg/pg of GAPDH for GB and 0.4 pg/pg of GAPDH for FasL and 0.8 pg/pg of GAPDH for P).

* Statistical analysis was performed with a $x^2$ test.

The magnitude of gene expression indicative for those genes associated with rejection, i.e., GB, P, and FasL, apparently declines after initiation of effective antirejection therapy (OKT3 or steroid pulses) as exemplified in the few sequential biopsy specimens analyzed (FIG. 2).

Posttransplant surveillance biopsies showed similar levels of IL-7, IL-10, IL-17, and GB transcripts as compared with nonrejecting kidneys, while early (day 4 and 11) posttransplant specimens revealed that IL-15, CTLA4, P, and FasL mRNA levels were 2- to 5-fold higher and showed a tendency to decline within the first week. In a limited sampling, early posttransplant gene expression was not predictive for the later development of rejection episodes.

EXAMPLE 2

ANALYSIS OF PBMCS

In a study of 16 renal allograft recipients, PBMCs were isolated from whole blood and RNA extracted by a modified QIAGEN™ method. (QIAGEN Rneasy Blood Mini Kits, Cat. No. 74303, 74304 or 74305). The QIAGEN technique involves four steps: 1) a sample is combined with a suitable buffer for isolating RNA in the sample from the remaining components, e.g., 1 part whole blood, is mixed with 5 parts lysing buffer, wherein the blood cells are lysed and RNA released; 2) RNA in the sample is specifically bound to particles or a membrane; 3) the particles or membrane are washed to remove non-RNA components; and 4) the isolated RNA is eluted from the particles/membrane.

To increase the efficiency of RNA isolation from PBMCs, the second step of the QIAGEN protocol was modified as described in Example 3.

Gene expression was analyzed by reverse transcription-assisted semi-quantitative PCR in PMBC and in snap frozen transplant core biopsies and was compared to the histopathological results (AR=12 and non rejecting NR=4). Coordinate gene expression in PBMCs and the AR grafts was noted in 11/12 (92%) for P, 10/12 (83%) for GB and 9/12 (75%) for FasL. Biopsy pathology could be accurately predicted by upregulation of at least 2 of the 3 genes in PBMCs in all cases. In the NR samples, false positive gene expression in PBMCs was noted in 2/4 (50%) for P, 2/4 (50%) for GB and 1/4 (25%) for FasL when compared with intragraft gene expression. The false positive PBMC results were obtained from 2 patients with CMV infection. Biopsy histopathology in the NR specimens was accurately predicted by non-expression of 2 of the 3 genes in PBMCs in the 2 patients without CMV infection. These results indicate that the evaluation of CTL gene expression in PBMCs with evaluation of markers for CMV can be used to assess the need for allograft biopsy and evaluate acute transplant rejection.

EXAMPLE 3

METHOD FOR PROCESSING BLOOD FOR PCR ANALYSIS

BLOOD COLLECTION

Supplies:
2 ml EDTA vacuum tubes (purple top): cat #369651 Vacutainer; Flask with ice.

Procedure:
Label EDTA tubes with Patient ID, date and time.

Draw 2 ml blood into EDTA tube and carefully mix by inversion; transport on ice to the lab to be processed.*

WHITE BLOOD CELL ISOLATION

Supplies:

3 cc syringes 15 ml Sterile Conical tubes (Falcon)—Sterile polypropylene tubes (20–200–1000 ul)

RPMI Medium 1640: cat #11875-085 Gibco BRL

EL Buffer: cat #79217 Qiagen

Flask with liquid nitrogen: cat #2123 Lab-Line.

Ethanol (96–100%) –70% ethanol in water 14.5 M β-Mercaptoethanol (β-ME)

Lab centrifuge with rotor for 15 ml tubes—4C

Microcentrifuge with rotor for 2 ml tubes

Instrumentation:

Lab centrifuge with rotor for 15 ml tubes at 4C.

Procedure:

1. Using a 3 cc syringe transfer 1–1.5 ml blood into 15 cc tube.
2. Mix the sample with 7.5 EL Buffer(1 ml/5 ml EL Buffer)
3. Incubate for 10–15 minutes on ice. Mix by vortexing briefly 2 times during incubation.

If the cloudy suspension does not become translucent, prolong incubation on ice to 20 minutes.
4. Centrifuge at 400×g for 10 minutes at 4C, check for pellet and discard all supernatant.

If pellet is red, incubate for an additional 5–10 minutes on ice after addition of EL Buffer at step 5.
5. Add 2 ml EL Buffer to the cell pellet. Resuspend cell using a pipet to carefully remove red cells. Add RPMI culture medium enough to fill 10 cc tube, place on ice.
6. Centrifuge again as in step 4, discard supernatant and make sure the pellet is completely clear of blood. If not, repeat step 5.
7. Place the tube with the pellet into the canister with liquid nitrogen to snap freeze.** Store at –70 Celsius.
8. Add 600 ul Buffer RLT (add 2ME) to pelleted while cells. Vortex or pipet to mix. No while cell pellet should be visible after this step.
9. Transfer lysis solution to Qiashedder column and spin 2 min 14–18.000 rpm.
10. Discard column and add equal amount of 70% ethanol to lysis solution and mix by pipetting.
11. Apply 500 ul to RNeasy column and spin 15 seconds with 10.000 rpm, discard flow-through and repeat with any remaining fluid.
12. Discard flow-through and pipet 700 ul Wash Buffer RW1 into spin column, centrifuge for 15 seconds 10.000 rpm and discard flow-through.
13. Place spin column in new 2 ml collection tube, pipet 500 ul of Wash Buffer RPE into column and centrifuge as above. Discard flow-through.
14. Pipet 500 ml of wash Buffer RPE into column and centrifuge for 2 minutes full speed to dry column; discard flow-through.
15. Transfer spin column to 1.7 ml Eppendorf tube and elute RNA with 30 ul of DEPC-treated or pure water. Spin for 1 minute 10.000 rpm. Repeat this step with 30 ul of water for further elution into the same collection tube.
16. Measure RNA by UV spectrometry and store at –70° C. If little or no RNA is eluted, again add 30 ul DEPC water to the spin column at room temperature for 10 min, then repeat step 15.

* For optimal results, blood samples should be processed within a few hours.
** This is a crucial step. RNA remains in snap frozen specimen stored at –70° C. However, it will rapidly degrade if the pellet defrosts or if snap freezing or storing is delayed.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

---

We claim:

1. A method of evaluating acute transplant rejection in a host comprising detecting upregulation of the expression of at least two immune activation marker genes in a post-transplantation fluid test sample comprising peripheral blood mononuclear cells, wherein the fluid test sample is selected from the group consisting of blood and lymphatic fluid and wherein the immune activation marker genes are selected from the group consisting of: perforin, granzyme B and Fas ligand, wherein upregulated gene expression of at least two of said immune activation marker genes indicates acute transplant rejection.

2. A method of evaluating acute organ rejection after transplantation in a host comprising determining the magnitude of gene expression of immune activation marker genes in a post-transplantation fluid test sample comprising peripheral blood mononuclear cells obtained from the host and comparing this magnitude to a baseline magnitude of gene expression of said immune activation marker genes, wherein the fluid test sample is selected from the group consisting of blood and lymphatic fluid, wherein heightened gene expression of at least two immune activation marker genes in the test sample indicates acute rejection, and wherein the immune activation marker genes are selected from the group consisting of: perforin, granzyme B and Fas ligand.

3. The method of claim 2 wherein the organ is a renal allograft.

4. The method of claim 2 wherein the gene expression is quantified by competitive reverse transcription polymerase chain reaction and the magnitude of gene expression is determined by calculating the ratio of the quantity of gene expression of each immune activation marker gene to the quantity of gene expression of a constitutively expressed gene.

5. The method of claim 4 wherein the constitutively expressed gene is glyceraldehydrate-3-phosphate dehydrogenase.

6. The method of claim 2 wherein the baseline magnitude of gene expression of the immune activation marker genes is calculated as the mean magnitude of gene expression from nonrejecting hosts, and heightened gene expression is determined as above a mean +/−95% confidence interval of these values.

7. The method of claim 2 wherein the baseline magnitude of gene expression of the immune activation marker genes is the magnitude of gene expression in a post-transplantation sample obtained from the host within 7 days of the transplantation and the post-transplantation test sample is obtained from the host more than 7 days after transplantation.

8. The method of claim 2 wherein the method additionally comprises detecting the presence or absence of an infectious agent in the sample, wherein heightened gene expression of two of the immune activation marker genes concomitant with the absence of the infectious agent indicates early organ rejection.

9. The method of claim 8 wherein the infectious agent is cytomegalovirus.

10. A method of evaluating acute transplant rejection in a host comprising determining the magnitude of gene expression of immune activation marker genes in a post-transplantation fluid test sample comprising peripheral blood mononuclear cells and comparing this magnitude to a baseline magnitude of gene expression of the immune activation marker genes, and detecting the presence or absence of infectious agent marker genes in the sample, wherein the fluid test sample is selected from the group consisting of blood and lymphatic fluid, wherein heightened gene expression of two of the immune activation marker genes in the fluid test sample concomitant with the absence of said infectious agent marker genes indicates acute transplant rejection, and wherein the immune activation marker genes are selected from the group consisting of: perforin, granzyme B and Fas ligand.

11. A method of detecting acute transplant rejection in a host comprising the steps of:
   a) obtaining a post-transplantation fluid biological sample comprising peripheral blood mononuclear cells containing immune activation marker genes and a constitutively expressed gene from the host, wherein the fluid biological sample is selected from the group consisting of blood and lymphatic fluid;
   b) isolating RNA from the sample thereby obtaining isolated RNA;
   c) obtaining complementary DNA from the isolated RNA;
   d) quantifying cDNA encoding the immune activation marker genes selected from the group consisting of perforin, granzyme B and Fas ligand and the constitutively expressed gene in the sample;
   e) calculating the ratio of the immune activation marker gene cDNA of step d) to the cDNA of the constitutively expressed gene to determine the magnitude of expression of the immune activation marker genes; and
   f) determining whether there is a heightened magnitude of expression of any two of the immune activation marker genes as compared to the magnitude of expression of the constitutively expressed gene;
      wherein a heightened magnitude of gene expression of at least two of the immune activation marker genes indicates acute transplant rejection.

12. The method of claim 11 wherein the constitutively expressed gene is glyceraldehydrate-3-phosphate dehydrogenase.

13. The method of claim 11 wherein the cDNA of step d) is quantified by competitive reverse transcription-polymerase chain reaction.

14. The method of claim 13 wherein perforin is amplified with oligonucleotide primers comprising the nucleotides of SEQ. ID. NO:17 and SEQ. ID. NO:18.

15. The method of claim 13 wherein granzyme B is amplified with oligonucleotide primers comprising the nucleotides of SEQ. ID. NO:19 and SEQ. ID. NO:20.

16. The method of claim 13 wherein Fas ligand is amplified with oligonucleotide primers comprising the nucleotides of SEQ. ID. NO:21 and SEQ. ID. NO:22.

17. The method of claim 12 wherein glyceraldehydrate-3-phosphate dehydrogenase is amplified with oligonucleotide primers comprising sequence of SEQ ID NO:1 and SEQ. ID. NO:2.

18. A method of screening for acute transplant rejection in a host comprising the steps of:
   a) obtaining a post-transplantation fluid biological sample comprising peripheral blood mononuclear cells containing immune activation marker genes selected from the group consisting of perforin, granzyme B and Fas ligand and constitutively expressed gene from the host, wherein the fluid biological sample is selected from the group consisting of blood and lymphatic fluid;
   b) determining the presence or absence in the sample a gene characteristic of an infectious agent marker; and
   c) determining whether there is a heightened gene expression of at least two of said immune activation marker genes, wherein said heightened gene expression in the absence of the infectious agent marker gene indicates acute transplant rejection.

19. The method of claim 18 wherein the host is a human host.

20. The method of claim 18 wherein the constitutively expressed gene is glyceraldehydrate-3-phosphate dehydrogenase.

21. The method of claim 18 wherein the infectious agent is cytomegalovirus.

22. A method of screening for the presence of acute transplant rejection in a host comprising the steps of:
 a) determining the magnitude of expression of at least two immune activation marker genes selected from the group consisting of perforin, granzyme B and Fas ligand genes in a post-transplantation fluid biological sample comprising peripheral blood mononuclear cells from the host by competitive reverse transcription polymerase chain reaction, wherein the
  fluid biological sample is selected from the group consisting of blood and lymphatic fluid; and
 b) comparing the magnitude of expression of at least two of said immune activation marker genes in the sample with a normal range of values of the expression of the genes;
  wherein the magnitude of the expression of any two of the genes of step a) that is greater than the magnitude of expression of the normal range of values indicates acute transplant rejection.

23. A method of assessing the efficacy of anti-rejection therapy during acute transplant rejection in a transplant host comprising the steps of:
 a) quantifying the magnitude of expression of at least two immune activation marker genes selected from the group consisting of perforin, granzyme B, and Fas ligand genes in a first fluid biological sample comprising peripheral blood mononuclear cells selected from the group consisting of blood and lymphatic fluid obtained from the host before administration of the therapy, thereby obtaining a pre-administration quantity of the expression of the transcripts of each gene;
 b) administering anti-rejection therapy to the host;
 c) quantifying the magnitude of expression of the genes in a second fluid biological sample comprising peripheral blood mononuclear cells selected from the group consisting of blood and lymphatic fluid obtained from the host after administration of the therapy, thereby obtaining a post-administration quantity for expression of the transcripts of each of the genes; and
 d) comparing the pre-administration quantity of the transcripts of each of said genes to the post-administration quantity of the transcripts of the same gene, wherein the post-administration magnitude of the transcripts of any two of said genes that is less than the pre-administration magnitude of the transcripts of the same two genes indicate the efficacy of the anti-rejection therapy during acute transplant rejection.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:1:

GGTGAAGGTC GGAGTCAACG      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:2:

CAAAGTTGTC ATGGATGACC                                              20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

CCTCTGGAGG AAGTGCTAAA                                              20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

ATGGTTGCTG TCTCATCAGC                                              20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

TTCTACAGCC ACCATGAGAA G                                            21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

CAGCTCGAAC ACTTTGAATA T                                            21

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

TTTAGGTATA TCTTTGGACT TCCTC                                        25

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

GTGTTCTTTA GTGCCCATCA A                                               21

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

TCTCTTGGCA GCCTTCCT                                                   18

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:10:

AATTCTCAGC CTCTTCAAAA ACTT                                            24

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

GCCGTGGAGC AGGTGAAG                                                   18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

AAGCCCAGAG ACAAGATA                                                   18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

CCGTGGCTTT GAGTAATGAG                                                 20

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:14:

CAGATTCTGT TACATTCCC                                                  19

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (xi) SEQUENCE DESCRIPTION: SEQ ID NO:15:

GGAGGCCATA GTGAAGG                                              17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (xi) SEQUENCE DESCRIPTION: SEQ ID NO:16:

GGGTCGGCTC TCCATAG                                              17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (xi) SEQUENCE DESCRIPTION: SEQ ID NO:17:

CGGCTCACAC TCACAGG                                              17

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (xi) SEQUENCE DESCRIPTION: SEQ ID NO:18:

CTGCCGTGGA TGCCTATG                                           18

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (xi) SEQUENCE DESCRIPTION: SEQ ID NO:19:

GGGGAAGCTC CATAAATGTC ACCT                                24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (xi) SEQUENCE DESCRIPTION: SEQ ID NO:20:

TACACACAAG AGGGCCTCCA GAGT                                24

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (xi) SEQUENCE DESCRIPTION: SEQ ID NO:21:

GCCTGTGTCT CCTTGTGA                                                      18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (xi) SEQUENCE DESCRIPTION: SEQ ID NO:22:

GCCACCCTTC TTTATACTT                                                  18

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:23:

CTGCGGATCT CTGTGTCATT                                            20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:24:

CTCAGAGTGT TGCTATGGTG                                            20

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (xi) SEQUENCE DESCRIPTION: SEQ ID NO:25:

CCAGAGCATC CAAAAGAGTG TG                                       22

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (xi) SEQUENCE DESCRIPTION: SEQ ID NO:26:

CTAGTTGGCC CCTGAGATAA AG                                       22

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:27:

GCAATGCACG TGGCCCAGCC                                      20

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (xi) SEQUENCE DESCRIPTION: SEQ ID NO:28:

TTTCACATTC TGGCTCTGTT GG                                 22

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:29:

CGGCACGCCT CGCTGTCATC                                      20

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:30:

TGTACTCCCG AACCCATTT                                       19

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (xi) SEQUENCE DESCRIPTION: SEQ ID NO:31:

TCCACGCTGT TTTGACCTCC ATAG                             24

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:32:

GACATCTTTC TCGGGGTTCT CGTT                             24